United States Patent [19]

Griffin et al.

[11] Patent Number: 4,740,072
[45] Date of Patent: Apr. 26, 1988

[54] VISION TESTING APPARATUS

[75] Inventors: Jan P. Griffin, Chesterfield; Anthony G. Gates, Colonial Heights; Delroy K. Rinehart, Chester, all of Va.

[73] Assignee: Titmus Optical, Inc., Petersburg, Va.

[21] Appl. No.: 823,784

[22] Filed: Jan. 29, 1986

[51] Int. Cl.<sup>4</sup> ............................................. A61B 3/02
[52] U.S. Cl. .................................. 351/243; 351/239; 351/244
[58] Field of Search ............... 351/200, 201, 239, 240, 351/243, 244, 245, 216, 233, 241, 242, 247

[56] References Cited

U.S. PATENT DOCUMENTS

| | | |
|---|---|---|
| 276,732 | 5/1883 | Trowbridge . |
| 1,669,916 | 5/1928 | Smith . |
| 1,949,067 | 2/1934 | Wheelock . |
| 2,091,173 | 4/1935 | Wottring . |
| 2,212,597 | 8/1940 | Haddad et al. . |
| 2,364,793 | 12/1944 | Jobe et al. . |
| 2,366,554 | 1/1945 | Peck et al. . |
| 2,485,272 | 10/1949 | Freeman . |
| 2,798,408 | 7/1957 | Ellis et al. . |
| 2,902,787 | 9/1959 | Cook . |
| 2,906,047 | 9/1959 | Cooke . |
| 3,011,394 | 12/1961 | Sherman et al. . |
| 3,012,472 | 12/1961 | Feinberg et al. . |
| 3,205,505 | 9/1965 | Fletcher et al. . |
| 3,416,856 | 12/1968 | Humphris . |
| 3,969,020 | 7/1976 | Lynn et al. . |
| 4,027,954 | 6/1977 | Good . |
| 4,146,311 | 3/1979 | Murr . |
| 4,155,632 | 5/1979 | Wolbarsht . |
| 4,301,195 | 11/1981 | Mercer et al. . |
| 4,365,872 | 12/1982 | Nunokawa . |
| 4,452,515 | 6/1984 | Lewis . |
| 4,536,065 | 8/1985 | Sheingorn . |
| 4,673,265 | 6/1987 | Haohe et al. . |

OTHER PUBLICATIONS

Besserman Flier, The First Automated, Self-Administered Vision Test System.
The VS-II Vision Screener Catalog from Keystone View.
The DVS-II Driver Vision Screening System Catalog from Keystone View.
The Keystone View 1984 Ophthalmic Products Catalog.
The Besserman Micro-Processor Automated Vision Test System Catalog.
The Sight Screener II Flier from AO Safety Products.

*Primary Examiner*—John K. Corbin
*Assistant Examiner*—Jay P. Ryan

[57] ABSTRACT

A vision tester having a casing horizontally adjustable with respect to a base. Inside the casing a rotating drum has a first end rotatably fixed to the casing and a second end unconnected to the casing and having an open portion. An illumination device is removably mounted to the casing and inserted inside the rotating drum through the open portion. The illumination device provides illunination to a plurality of test slides mounted to the surface of the rotating drum. A viewing device is mounted to the casing and provides left and right lenses simulating a far vision of the illuminated test slide. A pair of near vision lenses is rotatably mounted inside the viewing device and may be rotated to overlap the far vision lenses to simulate a near vision of the test slide. Peripheral vision is tested by light provided from an illumination source through fiber optic cables to peripheral vision test locations on the viewing device. A motor mounted within the casing drives the drum in accordance with commands input through a remote control unit. The rotating drum includes first and second cam wheels having registration devices which are detected by microswitches mounted to the casing. Position signals are output to the remote comtrol to display a signal indicating which test slide is being viewed. The test slide includes two glass layers with the test pattern negative and an opal glass sheet interposed therebetween. The test slide is temporarily retained on the rotating drum through a spring-clip mechanism.

32 Claims, 7 Drawing Sheets

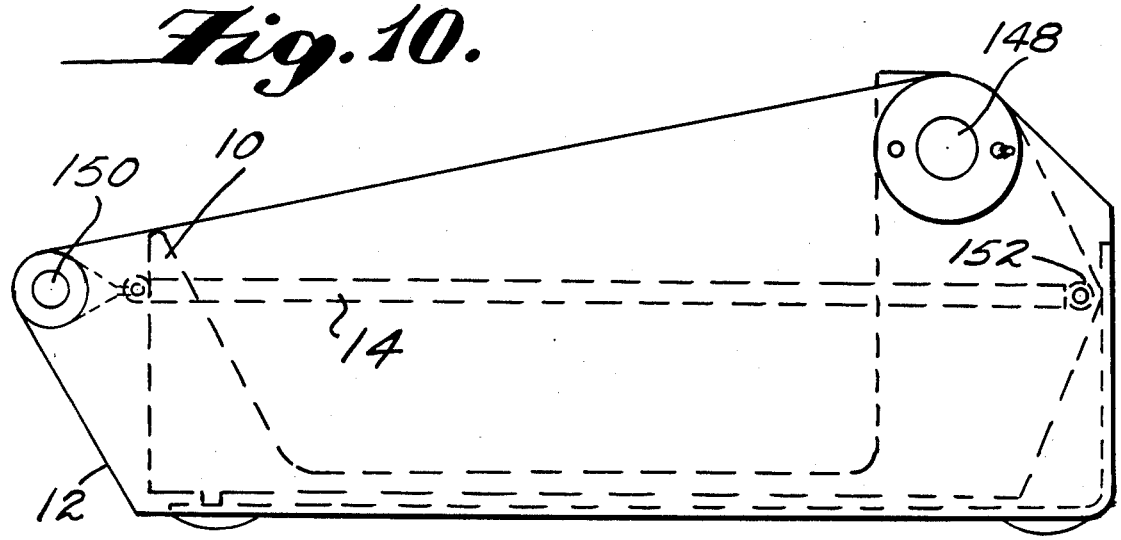
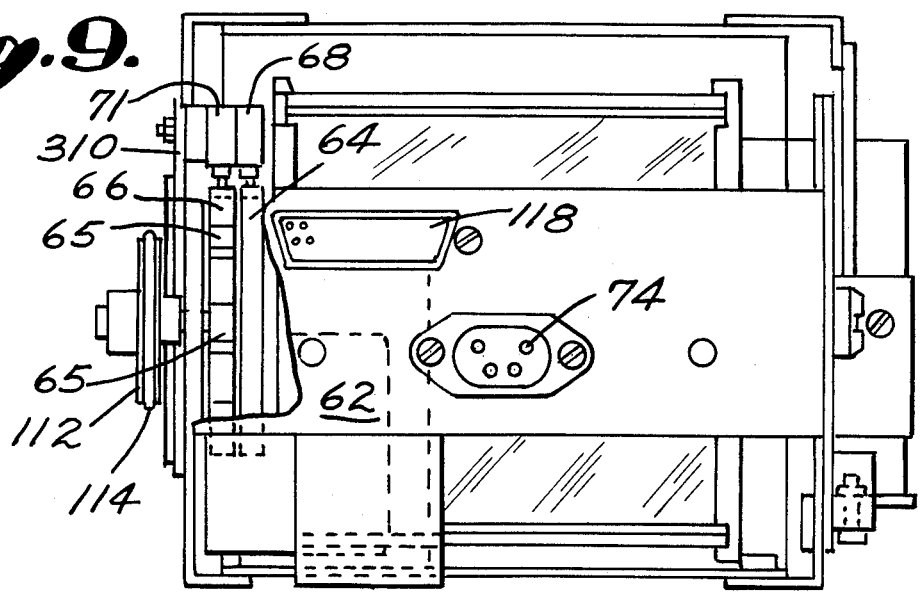
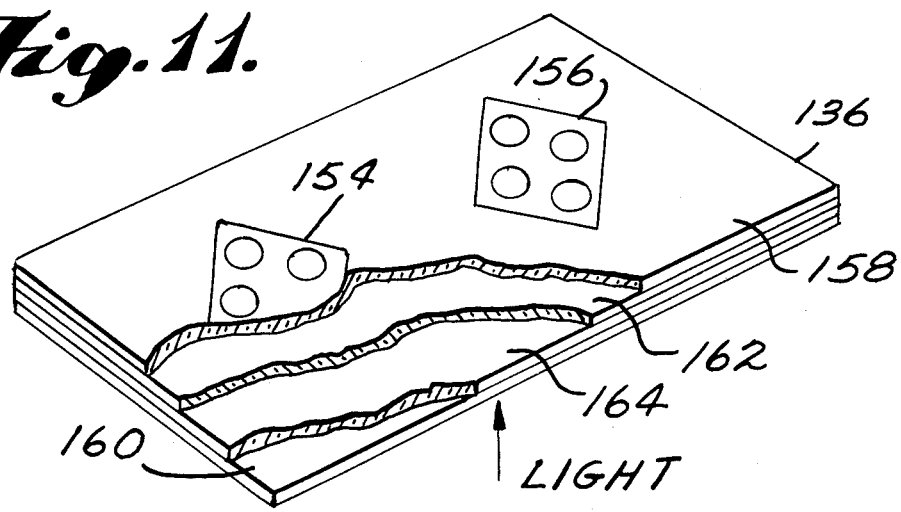

VISION TESTING APPARATUS

BACKGROUND OF THE INVENTION

The present invention relates to the field of ophthalmic instruments, and more particularly, to an improved, stereoscopic vision tester designed for rapid and precise measurement of visual performance, speed and ease of operation, and convenience of maintenance. The present invention is designed to provide a wide variety of standard vision tests in a small, compact, light-weight, portable instrument.

Eye testing devices are well-known for use in conducting limited testing of ophthalmic abilities of individuals. Such devices are particularly well suited for administering driver's license vision tests, mass screening of job applicants, and periodic vision testing of students. Devices of this type are described, for example, in such patents as U.S. Pat. No. 3,012,472 to Feinberg et al, U.S. Pat. No. 4,452,515 to Lewis, U.S. Pat. No. 4,027,954 to Good, U.S. Pat. No. 2,364,793 to Jobe et al, U.S. Pat. No. 2,798,408 to Ellis et al, and U.S. Pat. No. 3,205,505 to Fletcher et al.

The patent to Feinberg et al may be taken as representative of the types of devices presently available in the market. The eye testing apparatus according to Feinberg includes a light-occluding casing with a viewing device coupled thereto. The viewing device includes a headpiece and left and right lenses. Inside the light-occluding casing is a rotatable drum which holds a plurality of test slides on the drum surface. The drum is rotated by a handle extending through the side of the casing, and different test slides are thus presented to the person looking through the viewing device. The test operator rotates the drum, questions the test subject on the test slides he/she observes, and then manually records the test result.

The Feinberg device is also capable of testing near vision (approximately 14 inches) and far vision (approximately 20 feet). Within the drum are located four light bulbs. A first pair of light bulbs is positioned to illuminate a near test slide, while a second pair of bulbs is positioned to illuminate a far test slide. Each pair of bulbs includes a left and a right bulb. Within the viewing device is located a viewing frame which is angularly adjustable to alternately provide vision of the near test slide and the far test slide. The viewing frame is angled downward to view the near test slide in a direct optical path. The viewing frame is angled upward to view the far test slide after reflection of the test slide image from an optical mirror inside the casing. This reflection of the image increases the optical distance between the test subject and the far test slide to approximate far vision. Thus, the near/far test apparatus is complicated, bulky, requires four individual light bulbs, and a mirror which must be accurately positioned and kept clean.

Other near/far testing devices are known which include bifocal lenses inserted in the viewing device. Shutters are then manipulated to block either the top or the bottom of the bifocal lenses to switch between near and far vision. Such devices suffer from the same disadvantages of the Feinberg device.

Another disadvantage of the Feinberg device is the difficult maintenance required to change any of the light bulbs. The rotatable drum of Feinberg is coupled to the casing at both ends of the drum. Thus, to change a light bulb the apparatus must be disassembled and the drum must be removed from the casing. Therefore, replacing a light bulb requires a skilled maintenance technician and consumes a great deal of time. But, typically a vision tester of this sort is designed to be operated by relatively unskilled operators. Additionally, while handling the drum the test slides may become broken and/or marred, thus reducing vision test accuracy. Furthermore, to change a test slide on the rotating drum, the apparatus must again be disassembled further increasing maintenance cost and time.

Yet another disadvantage of the Feinberg device is the difficulty the test operator experiences in attempting to ascertain which test slide the test subject is observing. The device of Feinberg includes a viewing port cut into the side of the casing which allows a test operator to peer inside the machine to observe the same test slide as the test subject. Other known devices also include such ports cut into the casing at various locations to allow the test operator to confirm which test slide is being viewed by the subject. All such ports cut into the casing permit light to enter, thus obscuring the vision of the test subject. Such ports also may allow the entry of foreign materials which can cloud the test slides and degrade the performance of the moving parts.

A further disadvantage of devices such as Feinberg is the necessity for the test operator to position himself-/herself immediately adjacent the testing device. The test operator must manually rotate the test drum and frequently peer through the vision ports to confirm the observed test slide. This is disadvantageous in that the test subject may be made uneasy by the immediate presence of the test administrator. A vision tester which allows the test administrator to sit at a comfortable distance from the machine and the test subject would be very beneficial in aiding the accuracy of the test results.

Finally, such devices as Feinberg contain no means for testing horizontal visual field (peripheral vision). It is recognized that peripheral vision tests are very important to vision accuracy for driving and proper job performance. There are devices on the market which provide for peripheral vision testing by implanting a series of light emitting diodes (LEDs) in the headrest immediately adjacent the left and right viewing lenses. The LEDs are positioned at various angles with respect to the eye of the test subject. The LEDs are then selectively illuminated to determine the horizontal visual field of the test subject. A disadvantage of such known devices is that the implanted LEDs are very difficult to replace or service. Again, the eye testing apparatus must be disassembled and the LEDs must be removed from the very small space inside the headrest of the viewing device. An additional disadvantage of such known peripheral testing devices is that they may be easily circumvented by the test subject. Thus, the test subject can merely move away from the viewing lenses to more easily observe the LEDs implanted in the headrest. Thus, a test subject may have defective horizontal visual field yet still provide correct answers to the test operator.

With the rapid proliferation of computers in schools and offices, an increasing number of people are required to spend significant amounts of time operating computer terminals and observing a cathode ray tube. Such visual display terminal operators typically position themselves between 20 and 40 inches from the CRT. Since standard vision tests measure only near and far vision, vision problems occurring between 20 and 40 inches may disable some people from accurately operating a visual display terminal. Thus, it would be beneficial if vision testing devices could test the intermediate range of vision of each test subject. No known devices are capable of testing such intermediate vision.

Finally, no known devices are capable of being interfaced with a computer. Such a computer interface would be very beneficial to store the massive amounts of data inherent in a mass vision screening system. Thus, driver's license testing stations could interface each testing device to a computer which would store vision test records of each driver's license recipient. A few known vision testing devices include a computer as part of the apparatus. This computer aids in performing the test and provides a print-out of the test results. However, none of these known devices have a provision for optionally interfacing the vision test apparatus with any number of computers. Such a vision test apparatus could be accomplished by including a RS-232 interface in the vision testing device. Then, the vision tester could be interfaced with a wide variety of professional and personal computers.

Thus, from the above discussion, it is apparent that advances in technology and improved design could provide a vision testing device which is compact, provides accurate test results, allows convenient test administration, and is easy to maintain.

SUMMARY OF THE INVENTION

The object of the present invention is to provide an improved vision tester capable of overcoming the above-discussed problems, and providing a lightweight, compact, vision testing device which is easy to assemble, provides greater test precision, is easy to operate, and simple to maintain.

The present invention provides a vision tester having an advanced-design rotating drum located inside the casing. The rotating drum is mounted to only one side of the casing (cantilevered), and has an open passageway at its other end. A removable illumination module is inserted into the drum open end to provide backlight illumination of the test slide. The illumination module is temporarily fixed to the casing but is easily removable to allow convenient bulb replacement. Thus, the drum never has to be decoupled from the casing to change the light bulbs.

The test slides are temporarily fixed to the surface of the drum. Each slide is held on the drum by a spring-clip mechanism which can be manipulated to allow easy removal of the test slides. Thus, the test slides can be changed without decoupling the drum from the casing.

Another aspect of the present invention includes peripheral vision testing apparatus, including fiber optics. Illumination for the peripheral vision test is provided by a series of light bulbs located at a convenient location on the casing. The light is then piped from this illumination source to appropriate locations on the headrest through a plurality of fiber optic cables. Thus, changing a light bulb is accomplished at a convenient location not requiring disassembly of the headrest. The peripheral vision testing apparatus also includes a misalignment override switch having an emitter and a detector located on opposite sides of the headrest. When the test subject's head is fully positioned in the headrest, the emitter beam is broken and it is known that the test subject is properly positioned. If the beam is broken, illumination of the test slides in the drum is provided. However, should the test subject pull away from the headrest, the emitter beam will not be broken and the test slide will not be illuminated. This alerts the test operator and the test subject of a misalignment between the test subject and the headrest, and prevents cheating on the far/near and the peripheral vision test.

In another aspect of the invention, a motor is provided inside the casing and coupled so as to rotate the drum. The motor is controlled by a remote control device which also may be adapted to control the illumination module inside the drum and the peripheral vision testing apparatus. By operating the remote control, the test operator can position the drum so as to present predetermined slides to the test subject. Display means on the remote control itself inform the test operator which slides are being viewed by the test subject. Thus, no viewing port needs to be cut into the casing.

In order to determine the position of the rotating drum, the drum includes registration means and a registration-detecting device. Such means may conveniently include a first cam wheel and a second cam wheel coupled to the end of the drum. The first cam wheel includes a single detent which is placed adjacent a predetermined test slide, number 1. The second cam wheel includes a plurality of detents, each located adjacent a respective test slide. First and second microswitches have levers which ride on the cam wheels and provide output signals indicating when the first test slide is at the viewing position, and when the other test slides are at the viewing position. These signals are output to the remote control which can then display the exact test slide being observed by the test subject.

Another aspect of the present invention is the inclusion of a computer interface device inside the vision test apparatus. This device may include a RS-232 interface capable of inputting information into a wide variety of professional and personal computers.

Another aspect of the present invention includes a novel system for providing near and far vision testing. The lenses fitted into the viewing apparatus are adapted to provide a far view (simulating 20 feet) of the test slide. A second set of lenses is adapted to be positioned immediately behind the far lenses, and are adapted to provide near vision (simulating 14 inches) of the test slide. Thus, the test subject looks at the same slide through the same optical path to test for both near and far vision. The near lenses may be mounted on a horizontal axle in the viewing device and may be rotated into position behind the far lenses by the manipulation of a lever fixed to the end of the axle and located on the outside of the casing. Thus, simple rotation of the lever will rotate the near lenses into and out of position behind the far lenses.

In another aspect of the present invention, means are provided for testing the intermediate range vision of the test subject. For this test, a series of supplemental lenses are positioned immediately behind the far lenses, and are adapted to simulate intermediate vision (20–40 inches). A supplemental lens port is provided in the viewing device immediately above and behind the far lenses. The supplemental lenses may then be inserted and dropped into the proper position. To ensure that the supplemental lenses are not inserted while the near lenses are in position, the supplemental lens port is located immediately above the axle holding the near lenses. A supplemental passageway is then provided in this axle in only one direction. Thus, where the near lenses are rotated away from the far lenses, the supplemental passageway will register with the supplemental port, and the supplemental lenses can then be dropped into position. If the near lenses are rotated down behind the far lenses, the supplemental passage will not register with the supplemental port and the supplemental lenses cannot be inserted through the axle.

In another aspect of the present invention, the remote control is provided with advanced software to make test administration much easier. For example, the remote control may automatically reset the vision testing device upon power-up. Thus, the drum will be automatically rotated to present the first slide to the test subject, the peripheral vision testing apparatus may be automatically set to test the right eye, the illumination inside the drum may be switched to bright (day) illumination, and illumination to both left and right portions of the test slide may be provided.

In another aspect of the present invention, test slides are provided which aid in the accuracy and precision of the vision test. Each slide includes first and second glass layers with a test pattern negative interposed between the glass layers. Also interposed between the glass layers, and adjacent the test pattern negative is a sheet of light diffusing material (opal glass) to properly diffuse the light passing through the test pattern negative. The opal glass layer may also be formed integrally with one of the glass layers. By providing the opal glass immediately adjacent the test pattern negative, excellent light diffusion is accomplished, thus increasing the accurate perception of the test slide.

BRIEF DESCRIPTION OF THE DRAWINGS

The advantageous structure according to the present invention will become further apparent from the following detailed description of the presently preferred exemplary embodiment, when taken together with the drawings, in which:

FIG. 9 is a rear elevation view of the apparatus with parts broken away for clarity to illustrate the cam and position detecting switches;

FIG. 10 is a side elevation view of the casing showing the counter-balance spring mechanism; and FIG. 11 is a perspective view of the test slide, partially in section.

DETAILED DESCRIPTION OF THE PRESENTLY PREFERRED EXEMPLARY EMBODIMENT

Figure 1:
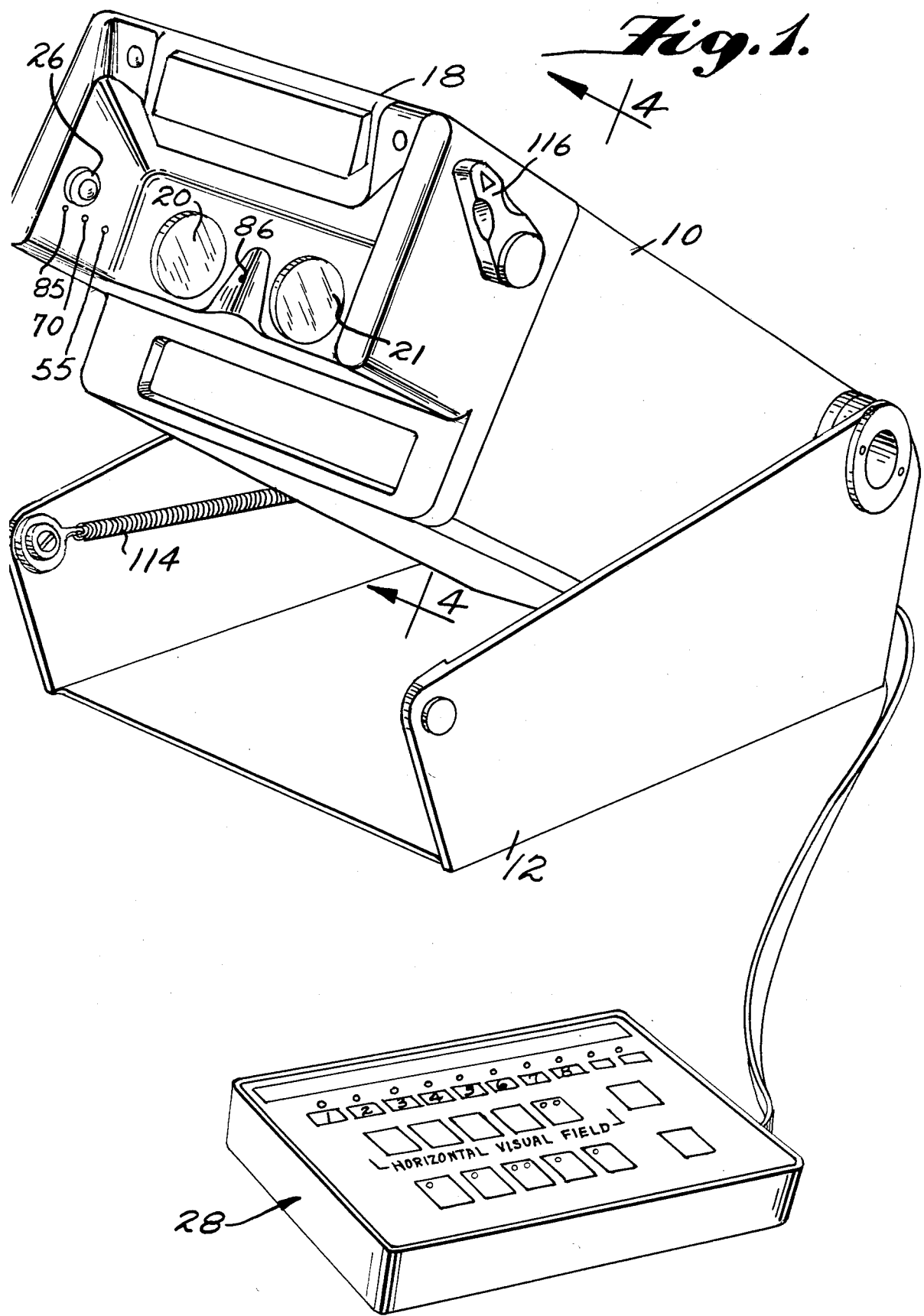
FIG. 1 is a perspective view of the device according to the present invention.

Before entering into a detailed description of the apparatus according to the present invention, a brief narrative of a typical vision test will be provided to aid in understanding the description of the apparatus. This test narrative will be given with reference to FIGS. 1 and 2.

The test subject is positioned adjacent the apparatus and casing 10 is pivoted upward from base 12 to a position which most easily accommodates the test subject. Counter-balance spring 114 will then maintain the casing at the selected angle. The test operator then presses power button 41 on the keyboard of remote control 28 to power-up the system. On power-up, the drum holding the test slides (see FIG. 7) is automatically rotated to position test slide number 1 at the viewing position.

After pressing the power button, the test operator observes the remote control to confirm that the display light 42 on the power key is turned on; the display light 32 over the test slide number 1 label is turned on; the horizontal visual field left/right key 38 has the display light 40 on over the R; the over-ride display light 44 is off; the day/night illumination key 45 has the display light 46 over the D turned on; and both the left and the right occlude display lights 50,51 are off.

The test operator then positions the near/far lever 116 in the far position and asks the test subject to place his/her head up to viewing device 18 and view test slide number 1 through lenses 20 and 21. The test subject inspects test slide number 1 and answers a series of questions posed by the test administrator. Typically, test slide number 1 will test the ability of the test subject to fuse his/her eyes.

Next, the test administrator presses advance button 52 on the keyboard which causes the motor to rotate the test drum to present slide number 2 to the test subject and to cause the display light 32 over the test slide number 2 label to turn on. The test subject then answers a series of questions with respect to test slide number 2. In a like fashion, the test administrator continues to press the advance button on the keyboard to rotate the drum through all eight test slides. Should the test subject have difficulty with any given slide, the test administrator can occlude either the left or the right portion of the test slide. This is accomplished by pressing the left or the right occlude key 48,49 on the keyboard. This will turn off the light on either the left or the right side of the drum and thus darken that portion of the test slide.

Should the test subject have difficulty in fusing his vision on any given slide, the test administrator can press the reset button 53 on the keyboard to automatically rotate the drum to return test slide number 1 to the viewing position. The test subject can then properly fuse his vision with the fusion vision test slide.

If desired, the test subject's night vision can be tested by pressing illumination key 45 on the keyboard to cause display light 47 over the N to turn on. This will reduce the amount of illumination provided by the illuminating device inside the drum, thus simulating the lower light levels of night viewing.

Upon completion of the far tests, the test administrator rotates lever 116 to the near position. This causes the near vision lenses to be rotated down behind far vision lenses 20,21 and present a compound lens system. Now, the test subject's vision of the test slide will simulate near vision. The test administrator hits reset key 53 to return test slide number 1 to the viewing position. Then, the near vision tests are performed in the same manner as the far vision tests described above. Again, the test administrator may occlude either eye, provide day/night illumination levels, and reset the drum to test slide number 1, if required.

Upon completion of the near vision tests, the test administrator may perform intermediate vision tests with a supplemental lens. The test administrator rotates the near/far lever 16 to the far position and then inserts a supplemental lens device 102 through a top of viewing device 18 through the supplemental lens port 100 (see FIG. 5). Thus, the test subject is presented with a compound lens system simulating intermediate vision. The test administrator presses reset button 53 to return test slide number 1 to the viewing position. The test administrator then re-performs tests on the eight slides, as described above.

The last test to be performed may be the peripheral vision test. The test administrator selects an appropriate slide to be observed and then asks the test subject to move his/her head up to viewing device 18. The test subject is then asked to observe the test slide while the test administrator presses horizontal visual field left/right key 38 to test either the left or the right eye. Then, the test administrator presses 85° key 34 which causes a light to appear at peripheral vision location 85. If the test subject sees this light, it is determined that his/her peripheral vision is normal. If light is not seen at location 85, the test administrator proceeds to press 70° key 35 which causes a light to appear at location 70. If the test subject still does not observe light at location 70, the test adminstrator presses 55° key 36 to cause a light to appear at location 55. After the outside peripheral vision is tested, the test administrator presses N key 37 to cause light to appear at nasal peripheral vision location 86. Thus, the inside peripheral vision of the test subject is tested.

In order to ensure that the test subject is properly positioned with respect to viewing device 18 (during peripheral vision testing and during far/near vision testing), an emitter-detector override apparatus is mounted within viewing device 18. Radiation is emitted from emitter 26 to detector 24 (not shown). If detector 24 is receiving radiation, this indicates that the test subject's head is not properly positioned with respect to viewing device 18. In this case, the illumination device within the drum is caused to turn off to halt the test. If the test subject's head is properly positioned, detector 24 will receive no radiation and the illumination device within the drum will remain on.

Should the test administrator desire to test a subject whose head is positioned away from viewing device 18 (for example where the test subject is wearing glasses), the test administrator can hit override key 43 on the keyboard to disable the emitter-detector override switch mechanism. This will allow the illumination within the drum to remain on all the time.

At the conclusion of the test, the apparatus may be turned off by pressing power button 41 on the keyboard, and casing 10 may be rotated downward into the compact storage position.

If the vision test apparatus is coupled to a computer, the test results may be automatically stored on a storage device prior to completion of the test.

Now, a detailed description of the structure and functions of the present invention will be provided.

FIG. 1 shows a perspective view of the apparatus according to the present invention. Casing 10 is pivotally mounted to base 12 and may be adjusted to a convenient viewing angle. Counter-balance spring 114 maintains the angle between casing 10 and base 12. Viewing device 18 is coupled to casing 10 and includes left lens 20, right lens 21, emitter 26, detector 24 (not shown), near/far lever 16, and the peripheral vision testing locations 55, 70, 85, and 86. Keyboard 28 is coupled to control circuitry inside casing 10 via ribbon cable 30.

As used in the specification and claims, the phrase "coupled to" means that one member is connected to another. The connection may be mechanical or electrical, direct or indirect; or accomplished by permanent or temporary fixing means. Thus, the remote control is electrically "coupled" to the device within the casing by an electrical wire. Likewise, the rotating drum is mechanically "coupled" to the casing by being mounted on an inner casing which is, in turn, mounted to the outer plastic shell of casing 10. The phrase "coupled to" is thus defined to cover means of connecting members together, which means would suggest themselves to persons having ordinary skill in this field.

Figure 2:
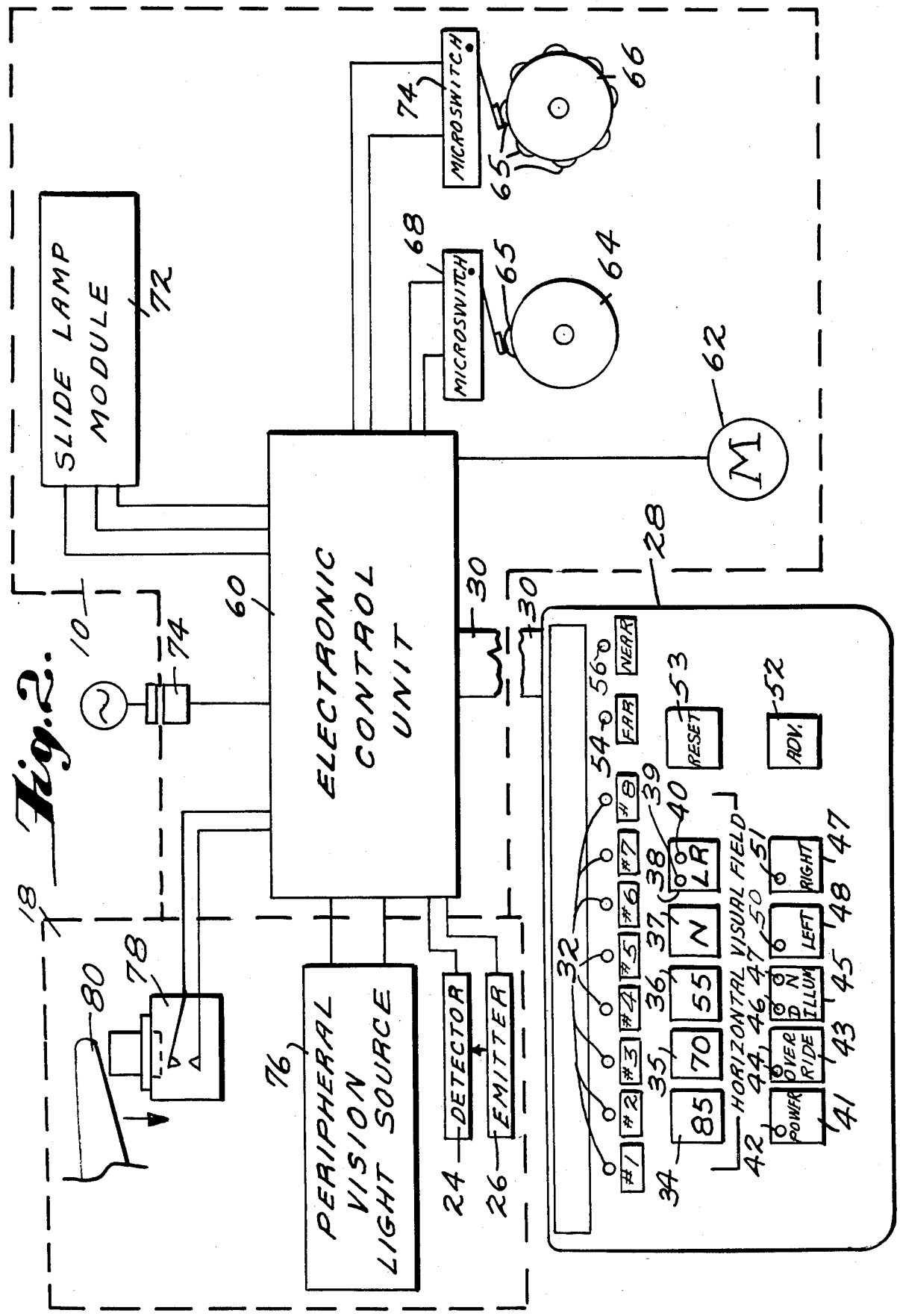
FIG. 2 is an electrical block diagram of the present invention, including the keyboard.

FIG. 2 is a block diagram depicting the main electrical components of the apparatus according to the present invention, together with a detailed diagram of remote control keyboard 28.

Remote control keyboard 28 displays a number of keypads and indicator lights used for testing, as described above. The keyboard includes membrane switches covered by a relatively smooth, wear-resistant plastic material to protect the circuitry inside the keyboard and to promote long life of the switches. Display lights 32 are located adjacent to individual test slide labels and are respectively illuminated to indicate which test slide is present at the viewing position. The horizontal visual field switches are indicated at 34–38 and include an 85° switch 34, a 70° switch 35, a 55° switch 36, a nasal switch 37, and a left/right switch 38. The left/right switch 38 includes display lights 39 and 40 for displaying which eye is being subject to peripheral vision testing.

Pressing power switch 41 will alternately power-up and power-down the apparatus. Power switch 41 includes display light 42 which, when lighted, indicates that the apparatus is powered-up. Override switch 43 can disable the emitter-detector override switch mechanism to provide constant illumination inside the drum, as described above. Display lamp 44 indicates whether the override key has been pressed.

Day/night illumination switch 45 alternately switches the illumination source inside the drum between a bright (daylight) and a less bright (night) illuminating condition. Display lights 46 and 47 show the illumination condition of the illumination device.

Left occlude switch 48 and right occlude switch 49 may be pressed to occlude vision in the left or right eye. This is accomplished by switching off one of the two light bulbs in the illumination device located inside the drum. Display lights 50 and 51 show the occlusion condition of the illumination device.

Advance switch 52 is depressed to rotate the drum by one test slide. Reset key 53 is depressed to rotate the drum until the first test slide is at the viewing position. Finally, far display light 54 and near display light 56 indicate the position of near/far lever 16.

FIG. 2 also shows the main electrical components within casing 10 and viewing device 18. Casing 10 includes electronic control unit 60 for synchronizing and coordinating all the electrical components. Electronic control unit 60 also includes the active and passive electronic components necessary to communicate with remote control 28.

Motor 62 is controlled by electronic control unit 60 and drives the rotating drum. The motor may, for example, be an AC motor capable of stepper operation.

The first cam wheel 64 and the second cam wheel 66 are both coupled to the end of the rotating drum. Cam wheel 64 includes a single registration device 65 while cam wheel 66 includes a plurality of such devices. These registration devices may include cams, detents, optically distinguishable features, or other devices capable of being positionally distinguishable. A first microswitch 68 is positioned so as to detect the registration device on cam wheel 64, while microswitch 71 is positioned to detect the plurality of registration devices on cam wheel 66. Again, devices 68 and 71 may also include any detecting means capable of distinguishing the registration devices on cam wheels 64 and 65.

Slide lamp module 72 is inserted within the rotating drum and provides back illumination of the test slides positioned on the surface of the drum.

Power plug 74 provides power to the system and is adapted to be connected to an AC outlet. It is to be understood that the apparatus according to the present invention may be powered by any convenient means.

Viewing device 18 includes peripheral vision light source 76 which provides the illumination necessary to test peripheral vision. Override switch emitter 26 provides illumination to detector 24 to properly position the test subject during peripheral vision testing. Finally, near/far switch 78 is activated by cam 80 which is coupled to near/far lever 16. Near/far switch 78 provides a signal indicating the position of near/far lever 16.

Turning now to FIGS. 3, 4, 5, and 6, a detailed description of the structure of viewing device 18 will be provided. Viewing device 18 includes a headrest casing 181 which is preferably made of molded plastic. Headrest casing 181 is preferably black to reduce reflected ambient light.

Figure 3:
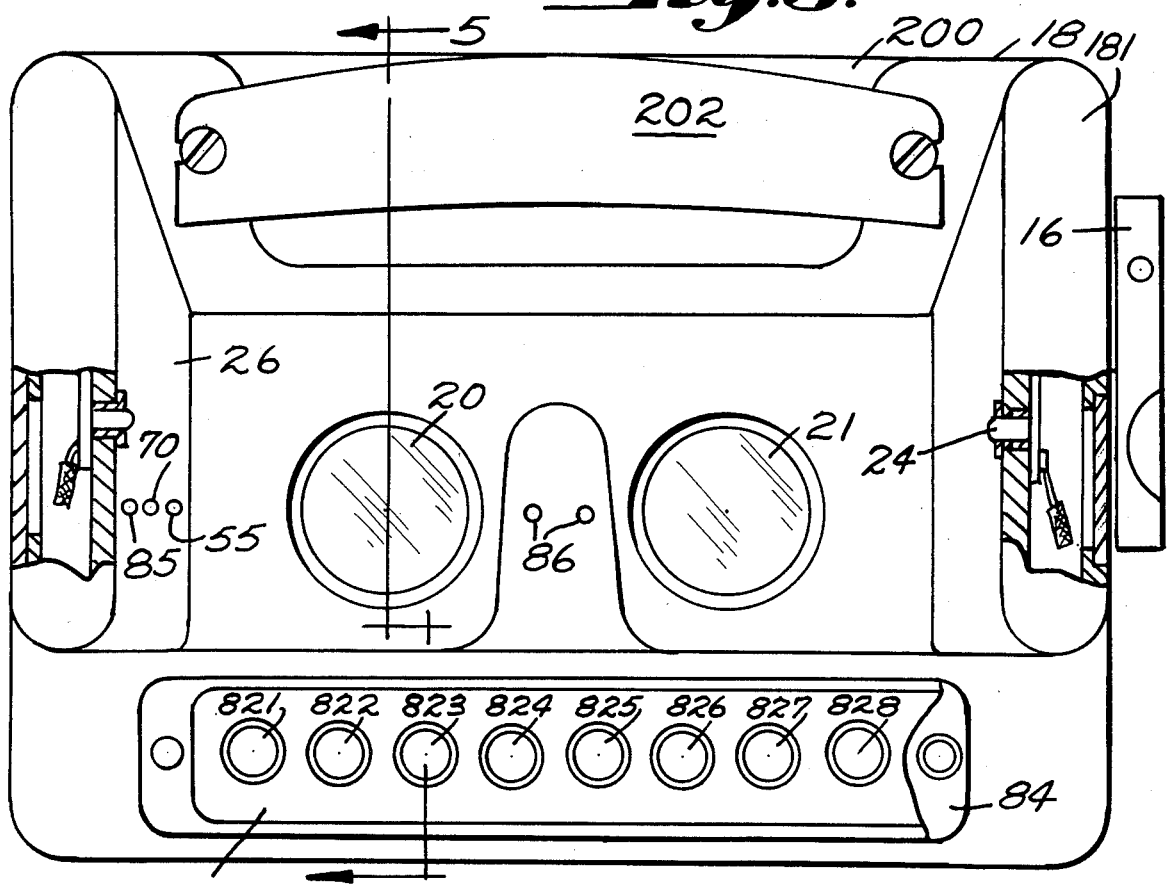
FIG. 3 is a front elevation view of the viewing system.

FIG. 3 depicts left far lens 20 and right far lens 21. These lenses provide a viewing station from which the selected test slide may be observed. Each of these lenses includes an optical axis which intersects the test slide located at the viewing position. At the top of viewing device 18 is located a head cushion 200 which may be covered by a pad of sanitary papers 202, in a well-known manner.

Figure 4:
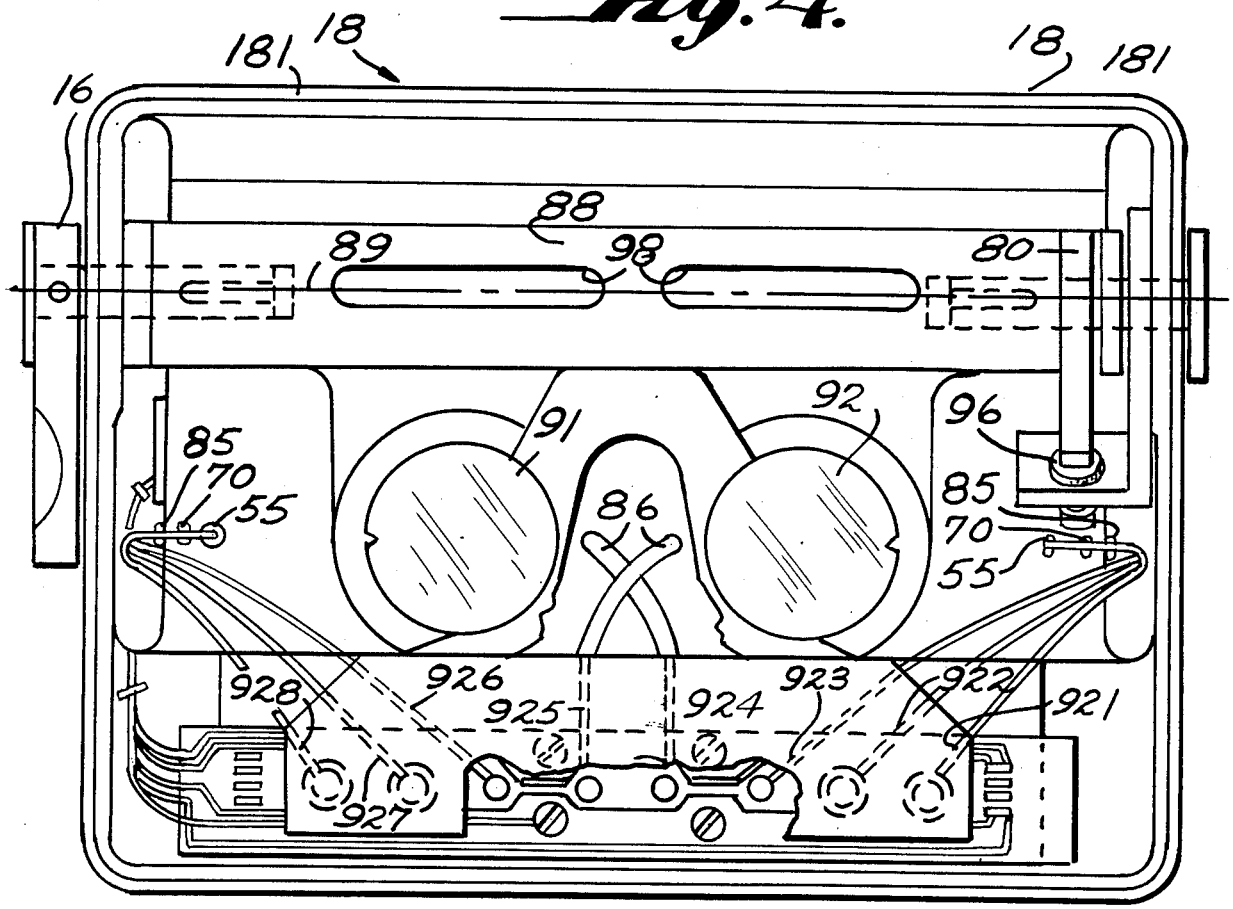
FIG. 4 is a rear elevation view of the viewing system taken along line 4—4 of FIG. 1.
Figure 6:
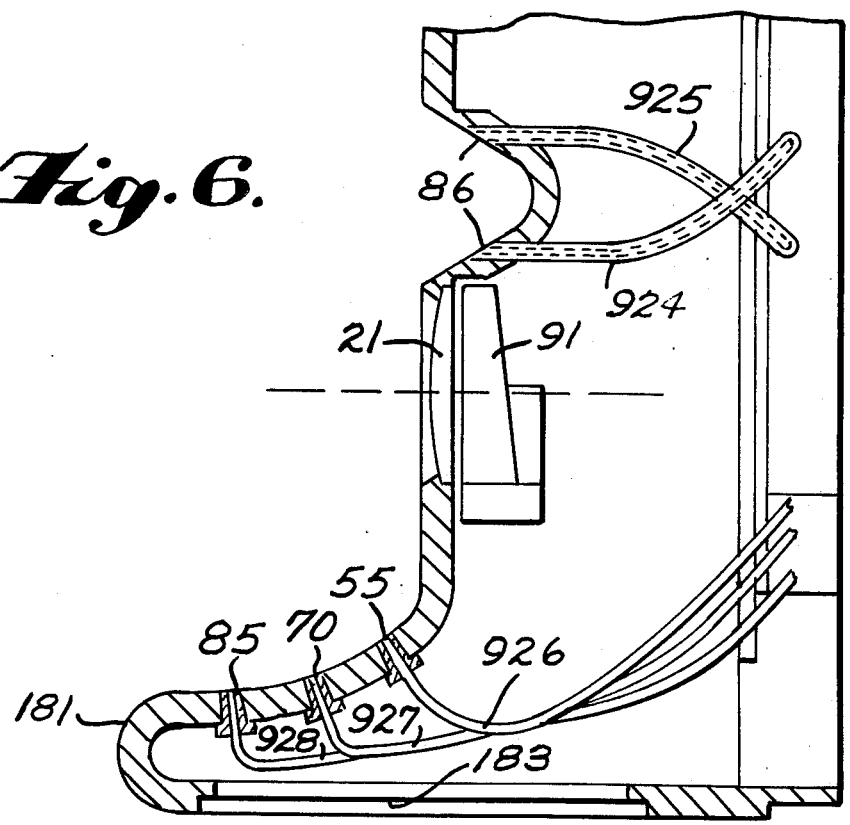
FIG. 6 is a fragmentary sectional view of the viewing system taken along line 6—6 of FIG. 1.

At the bottom of the viewing device 18 is located a peripheral vision illumination source 82. Illumination source 82 includes a plurality of lights 821-828 for providing illumination to the peripheral vision test locations 55, 70, 85, and 86. FIGS. 4 and 6 show that the light from illumination source 82 is carried to the peripheral vision test locations via a plurality of fiber optic cables 921-928. A fiber optic cable is affixed to each location 55, 70, 85, and 86. FIGS. 4 and 6 depict that the fiber optic cables affixed to locations 86 are shrouded to prevent light transiting fiber optic cables 924,925 from interfering with the vision of the test subject. While a plurality of illumination sources are depicted within the illumination source 82, it is to be understood that any convenient means of illumination may be provided.

The location of illumination source 82 is particularly convenient for replacing burned out light bulbs. Illumination source 82 is located immediately behind a removable panel 84 which is coupled to viewing device 18. Thus, maintenance of the peripheral vision device is very easy.

FIG. 3 clearly shows emitter 26 and detector 24 which are used to detect test subject misalignment during the peripheral vision tests and the far/near vision tests. Emitter 26 provides a radiation beam (light, infrared, sonic, etc.) to detector 24. When detector 24 receives this beam, it provides a signal to electronic control unit 60 which then switches off slide lamp module 72 to stop illumination of the test slide.

As depicted in FIG. 6, viewing device casing 181 may include access ports 183 located on each side of the headrest. Access ports 183 may be used to provide easy access to locations 85, 70, 55, and the fiber optic cables affixed thereto. Access ports 183 also provide easy access to emitter 24 and detector 26. Thus, maintenance of viewing device 18 is very convenient.

Figure 5:
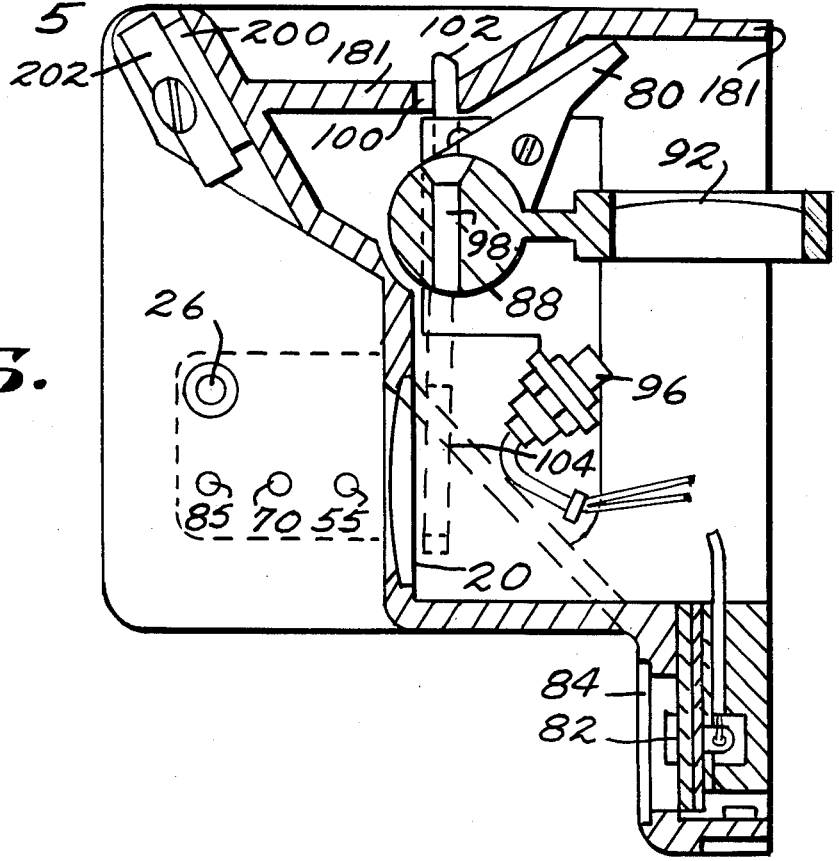
FIG. 5 is a sectional view of the viewing system taken along line 5—5 of FIG. 3.

FIGS. 4 and 5 depict the near vision testing apparatus and the intermediate vision testing apparatus. FIG. 4 is a rear elevation view of viewing device 18, as removed from casing 10. FIG. 5 is a cross-sectional view of viewing device 18 taken along 5—5 of FIG. 3. FIG. 4 shows near/far lever 16 affixed to a horizontally mounted axle 88. Axle 88 is mounted to casing 181 and rotates about axis 89. A lens holding device 90 is eccentrically mounted to axle 88 and holds lenses 91 and 92. Lenses 91 and 92 are adapted to provide, together with lenses 20 and 21, a near vision of the test slide located at the viewing position (simulating near vision of 14 inches). As depicted in FIG. 4, lenses 91 and 92 have been rotated downward so as to cover lenses 20 and 21 so that the optical axis of lens 91 is substantially colinear with the optical axis of lens 21, and the optical axis of lens 92 is substantially colinear with the optical axis of lens 20.

When near/far lever 16 is rotated to the far position, axle 88 rotates about axis 89 and lifts lenses 91 and 92 until their optical axes are approximately perpendicular to the optical axes of lenses 20 and 21. FIG. 5 depicts such a configuration.

Cam 80 is mounted to axle 88 and rotates therewith. When near lenses 91 and 92 are rotated downward, as in FIG. 4, cam 80 contacts override switch 96. Override switch 96 then sends a signal to electronic control unit 60 indicating that the compound lens system is in the near vision position. The electronic control unit 60 then sends a signal through remote control unit 28 which illuminates display light 56. When near lenses 91 and 92 are rotated away from lenses 20 and 21, cam 80 moves away from override switch 96 (as depicted in FIG. 5) and switch 96 sends a signal to electronic control unit 60 which causes display light 56 to turn off and display light 54 to turn on. Override switch 96 is conveniently mounted to the inside of viewing device 18.

The apparatus for providing intermediate vision testing will now be described. Axle 88 includes a supplemental lens passageways 98 which pass through axis 89 in only a single plane (the plane orthogonal to the plane of the drawing of FIG. 4). Likewise, casing 181 includes a supplemental lens port 100 located at the top of the casing. As depicted in FIG. 5, when axle 88 is rotated counterclockwise until the optical axis of lens 92 is approximately perpendicular to the optical axis of lens 20, supplemental lens passages 98 register with supplemental lens port 100 allowing access to the area immediately behind lens 20. In this configuration, supplemental lens system 102 may be inserted from the top of viewing device 18 to place supplemental lens 104 immediately behind lens 20 so that they substantially share an optical axis. Supplemental lens 104 is especially configured to provide, in conjunction with lens 20, an intermediate vision of the test slide at the viewing position (simulating vision of 20-40 inches). When the intermediate vision tests are concluded, supplemental lens device 102 may be easily withdrawn. It is a novel feature of the present invention that supplemental lens device 102 may be installed only after lens 92 has been rotated out of position. Thus, viewing device 18 contains unique structure and novel apparatus for providing accurate and rapid vision tests.

Figure 7:
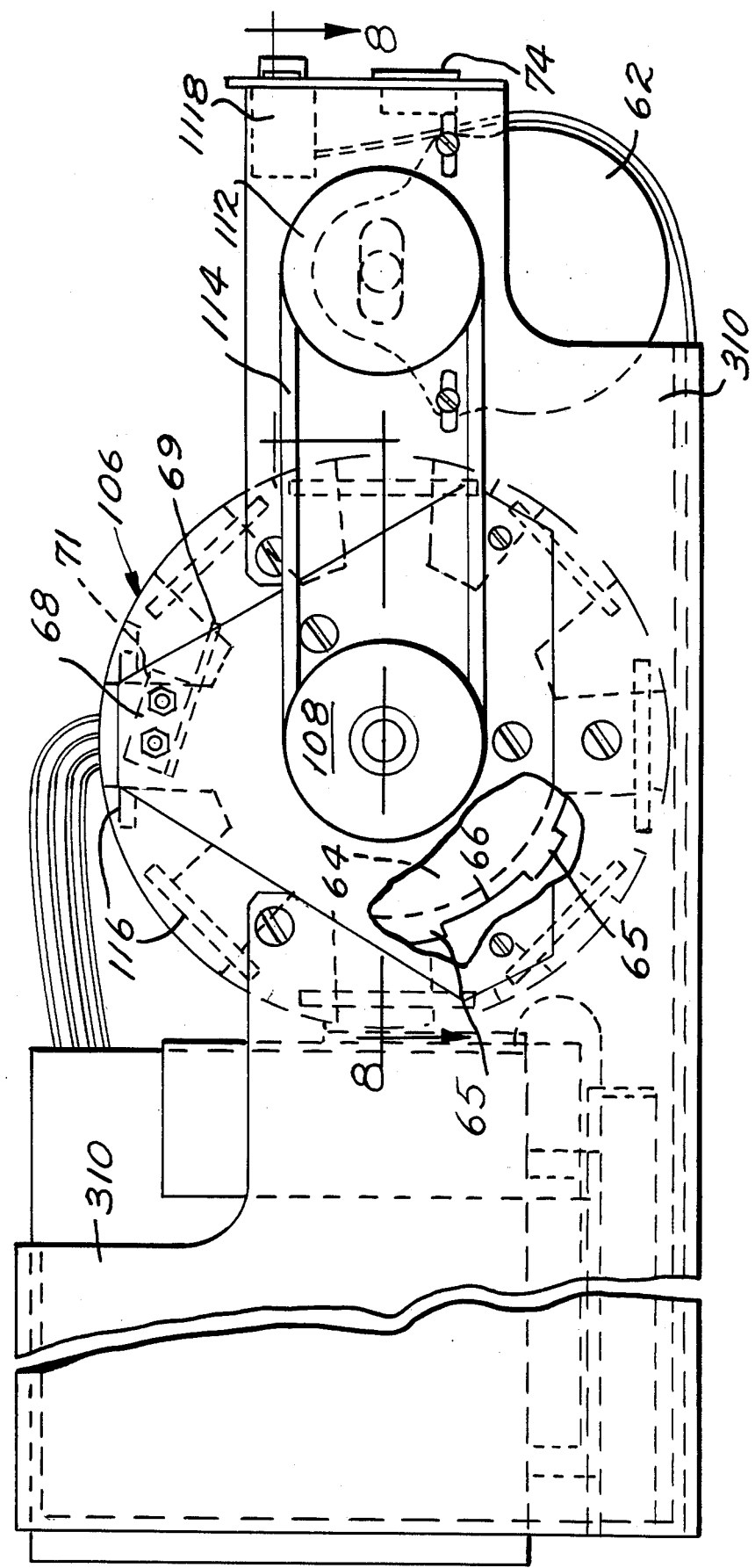
FIG. 7 is a side elevation view of the mechanism showing in detail the drum and driving mechanism.
Figure 8:
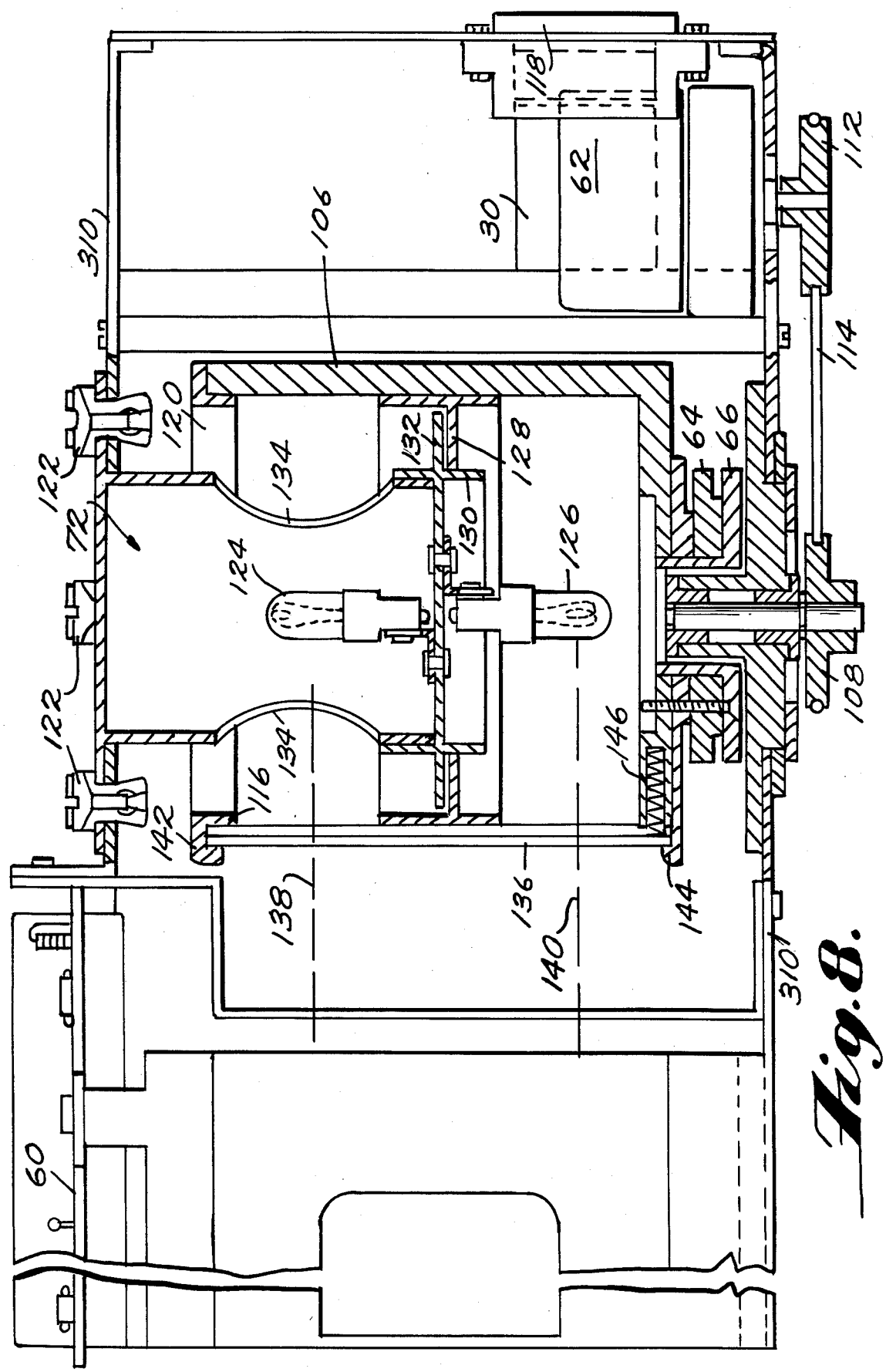
FIG. 8 is a sectional view of the apparatus taken along line 8—8 of FIG. 7.

Now, a description of the rotating drum and other components mounted to an inner casing 310 which is fixed within casing 10 will be provided with reference to FIGS. 7, 8, and 9. FIG. 7 is an end view of the rotating drum apparatus showing rotating drum 106 having a pulley wheel 108 affixed to one end thereof. Motor 62 has a pulley wheel 112 which is coupled to pulley wheel 108 through belt 114. Thus, motor 62 transfers drive force to rotating drum 106.

Rotating drum 106 is seen as being generally octagonal in cross-section, thus containing eight test object carrying stations 116. A test slide may be affixed to each of these test object carrying stations to provide a total of eight test slides on the rotating drum. It is to be understood that other numbers of test slides may be provided on rotating drum 106. Thus, rotating drum 106 can be hexagonal, pentagonal, etc. in cross-section. Alternatively, the test object carrying means may be other than a rotating drum and still conform to the teachings of the presently claimed invention. Thus, the test object carrying means may include a linear display, a curvilinear display, or a matrix display of test slides.

To the end of rotating drum 106 are affixed first cam wheel 64 and second cam wheel 66. As shown in the cut-away portion of FIG. 7, cam wheel 66 includes a plurality of registration devices 65. Each registration device 65 is located adjacent one of the test carrying stations 116.

Microswitches 68 and 71 are mounted to casing 10 and each contain a lever 69 which rides on cam wheel 64 and cam wheel 66, respectively. As the lever detects registration devices 65, microswitches 68 and 71 output a signal to electronic control unit 60 indicating the position of rotating drum 106. Electronic control unit 60 sends appropriate signals to remote control 28 to illuminate display lights 32 to indicate which test slide is present at the viewing position.

FIG. 7 also depicts ribbon connector plug 118 which is used to interface ribbon cable 30 between electronic control unit 60 and remote control 28. The ribbon cable 30 can thus be easily disconnected from the back of casing 10 in order to allow compact shipping and storage.

FIG. 8 is a cross-sectional view of the rotating drum apparatus taken along line 8—8 of FIG. 7. FIG. 8 shows that rotating drum 106 is mounted inner to casing 310 at only one end of the drum. The other end of the drum contains an open portion 120 and is not connected inner to casing 310. Thus, rotating drum 106 is cantilever mounted on inner casing 10.

Through opening 120, slide lamp module 72 is inserted. Slide lamp module 72 is temporarily fixed to inner casing 310 with temporary fixing means 122. Thus, to remove slide lamp module 72 from rotating drum 106, it is merely necessary to manipulate fixing devices 122 and slide the slide lamp module 72 out of rotating drum 106 through open portion 120. Thus, maintenance of the slide lamp module is made very easy. Slide lamp module 72 includes a left eye illumination bulb 124 and a right eye illumination bulb 126. Each bulb is specially constructed to be color free and to provide precise illumination of the test slide. Illumination bulbs 124 and 126 are switchable between a bright (day) illumination and a less bright (night) illumination. Thus, vision testing of day and night vision can be easily accomplished.

Rotating drum 106 contains a circular partition 128 into which shoulder 130 of slide lamp module 72 is inserted. Slide lamp module 72 contains a circular partition 132 which cooperates with partition 128 to prevent light from left eye illumination bulb 124 from reaching the area in which right eye illumination bulb 126 is inserted. Thus, when either illumination bulb 124 or 126 is extinguished to occlude vision to one eye, light from the other bulb will not interfere with the test. Likewise, slide lamp module 72 contains circular openings 134 to further shield illumination bulb 124.

FIG. 8 also depicts motor 62, motor pulley wheel 112, transmission belt 114, rotating drum pulley wheel 108, which provide rotation to rotating drum 106. Thus, rotating drum 106 rotates about stationary slide lamp module 72 to present the various test slides to the viewing position.

Coupled to the end of drum 106, are cam wheels 64 and 66, previously described.

Shown at 136 is a test slide temporarily fixed and test object carrying station 116. Test slide 136 will be more fully described in connection with FIG. 11. However, it should be noted that test slide 136 contains a left pattern viewable along optical axis 138, and a right pattern viewable along optical axis 140. The intersection of the test slide with optical axes 138 and 140 delineate the viewing position from which the test slide is observed.

Test slide 136 is mounted to rotating drum 106 by fixed clip 142, and movable clip 144. Biasing spring 146 is mounted within the casing of rotating drum 106 and positioned to bias test slide 136 away from test carrying station 116, (counterclockwise about fixed clip 142 in FIG. 8). Movable clip 144 retains test slide 136 on test object carrying station 116 against the biasing force of biasing spring 146. Clip 144 is movable (downward in FIG. 8) to release test slide 136 and allow it to be forced away from test object carrying station 116 by biasing spring 146. Thus, test slide 136 is easy to place in, and remove from, test object carrying station 116. This novel feature allows test slides to be easily changed, repositioned, or cleaned and replaced onto rotating drum 106. This process is made even more easy by the provision of a doorway (not shown) in the top of casing 10 directly above rotating drum 106. Through such doorway, easy access may be had to the test slides and the rotating drum. Such a doorway may be also beneficial to the test administrator who can physically insert a pointer through the doorway to point to particular images on any test slide.

FIG. 8 also depicts electronic control unit 60 mounted orthoganal to the plane of FIG. 8. Electronic control unit 60 is for example a printed circuit board containing the active and passive electronic devices required to control and synchronize the electrical operations of the apparatus. Electronic control unit 60 is affixed to a ribbon connector 30 which is connected to ribbon cable connector 118.

FIG. 9 is a rear view of the apparatus described in FIGS. 7 and 8. FIG. 9 shows motor 62, motor pully wheel 112, and transmission belt 114. Also shown are ribbon cable connector 118, and AC outlet plug 74. This plug is adapted to provide power to the apparatus for many standard AC power outlet. Microswitches 68 and 71 are mounted to inner casing 310 and ride upon cam wheel 64 and 66. The cut-away portion of FIG. 9 depicts cam wheel 64 and 66 together with registration devices 65.

FIG. 10 shows that casing 10 is pivotally mounted to base 12 at pivot connection 148. Counter balance spring 14 is connected to base 12 at connection point 150, and is connected to casing 10 at connection point 152. As casing 10 is rotated clockwise about pivot point 148, counter balance spring 14 stretches and acts to support the weight of casing 10 at the predetermined angle. Thus, the angle between angle casing 10 and base 12 may be adjusted for each test subject, and once adjusted by hand will temporarily remain in position throughout the test.

FIG. 10 also shows the compact nature of the apparatus according to the present invention. When casing 10 is fully depressed in base 12, the apparatus may be easily carried and stored.

The majority of the components according to the present invention are preferably made of molded plastic. For example, the viewing device casing 183, casing 10, rotating drum 106, and slide lamp module 72, may all be made of light-weight plastic to reduce the weight of the apparatus. Thus, a light-weight, compact device is provided which is capable of performing fast and accurate vision test.

FIG. 11 is a perspective view, partially in section of test slide 136. It can be seen that test slide 136 includes a left pattern 154 and right pattern 156. Test slide 136 includes optical glass layers 158 and 160. Between these glass layers, test pattern negative 162 and opal glass layer 164 are located. The opal glass layer may also be formed integrally with one of the glass layers. Test pattern negative 162 includes the test patterns 154 and 156. These patterns are constructed to provide very precise test patterns to the test subject.

Opal glass layer 164 is located adjacent test pattern negative 162. Opal glass layer 164 acts to diffuse the light entering through glass layer 160 from illumination bulbs 124 and 126. Diffusion layer 164 is particularly suited to provide clear and crisp images of the test patterns to the test subject. Thus, the light rays striking the eye of the test subject are parallel and are normal to the plane of opal glass layer 164. If this opal glass layer were not provided, the light rays striking the eye of the test subject would not be parallel since they all originate from a single point (the illumination bulb).

By providing opal glass layer 164 inside test slide 136 and adjacent to test pattern negative 162, a more accurate image of the test pattern can be obtained. If space were permitted between opal glass layer 164 and test pattern negative 162, light rays entering into this space could be reflected providing an unclear image. Also, ambient light could enter the space between opal glass layer 164 and test pattern negative 162 and further cloud the image striking the eye of the test subject.

This particular configuration of test slide 136 also avoids a problem encountered at the prior art where the opal glass layer was permanently fixed to the rotating drum. This prior art configuration caused difficulty in that the opal glass could be easily marred or dirtied thus reducing the crispness of the test image. In addition, a space was thus provided between the opal glass and the test pattern negative allowing light reflections and the introduction of ambient light to further cloud the test image. By providing the opal glass interposed between glass layers 158 and 160, the opal glass can be kept clean and kept in the most advantageous position to provide a precise test image.

Thus, what has been described above is a lightweight, compact, easily serviced and maintained vision testing device capable of producing fast and accurate test results to a wide a variety of test subjects, and with a wide variety of test functions. While the invention has been described in connection with what is presently considered to be the most practical and preferred embodiments, it is to be understood that the invention is not limited to the disclosed embodiment but, on the contrary, is intended to cover various modifications and equivalent arrangements included within the spirit and scope of the appended claims, which scope is to be accorded the broadest interpretation so as to encompass all such modifications and equivalent structures.

What is claimed is:

1. Vision test apparatus, comprising:
   a light-occluding casing;
   test object carrying means rotatably mounted in a cantilever fashion in said casing and having a first end rotatably coupled to said casing and a second end which is unconnected from said casing and has an open portion, said test object carrying means having a plurality of test object carrying stations adapted to carry vision test objects;
   illumination means, mounted in said casing and extending inside said test object carrying means through said open portion, for illuminating said test object carrying stations; and
   viewing means, connected to said casing, for providing a viewing station from which said test object carrying station is viewed.

2. Apparatus according to claim 1 wherein said viewing means includes a left eye viewing port and a right eye viewing part, and wherein said illuminating means includes left and right eye illuminating means for alternately illuminating a test object carrying station to cause it to be alternately visible from said left and right eye ports, respectively.

3. Vision test apparatus, comprising:
   a light-occluding casing;
   test object carrying means mounted, within said casing in a cantilever fashion and having a plurality of test object carrying stations, adapted for carrying a plurality of test objects;
   viewing means, coupled to said casing, for providing a viewing station from which one of said test object carrying stations is viewed; and
   peripheral vision testing means, coupled to said casing, for testing peripheral vision, said peripheral vision testing means including an illumination source and fiber optic means for carrying light from said illumination source to a location on said viewing means from which peripheral vision is tested.

4. Vision test apparatus, comprising:
   a light-occluding casing;
   test object carrying means mounted to said casing and having a plurality of test object carrying stations, adapted for carrying a plurality of vision test objects;
   viewing means, coupled to said casing. for providing a viewing station from which said test object carrying means is viewed;
   motor means, coupled to said test object carrying means and to said casing, for positioning said test object carrying mènas to orient respective ones of said test object carrying stations with said viewing means;

position detecting means, coupled to said casing, for detecting which of said test object carrying stations is oriented with respect to said viewing means, said position detecting means including a cam wheel coupled to said test object carrrying means, for indicating a position of said test object carrying stations;

control means, coupled to said motor means and said position detecting means, for controlling said motor means to orient test object carrying stations with respect to said viewing means in a predetermined order; and computer interface means, mounted on said casing and coupled to said control means, adapted for interfacing said control means to a computer.

5. Apparatus according to claim 4 wherein said computer interface means includes an RS 232 interface.

6. Vision test apparatus, comprising:

a light-occluding casing;

test object carrying means, mounted within said casing and having a plurality of test object carrying stations, adapted for carrying a plurality of vision test objects;

viewing means coupled to said casing and positioned to provide a viewing station from which said test object carrying means is viewed, said viewing means including a left eye viewing port having a first lens with a first optical axis, and a right eye viewing port with a second lens having a second optical axis;

compound lens means for alternately providing a near and a far vision of said test object carrying station from said viewing means, said compound lens means having third and fourth lenses with third and fourth optical axes respectively, said compound lens means being switchable between a first position where said third and fourth optical axes are substantially colinear with said first and second optical axes respectively, and a second position where said first and second optical axes do not intersect said third and fourth lenses; and compound lens manipulation means having a horizontal axis, for moving said compound lens means from a horizontal to a vertical position to provide one of said near and far vision.

7. Vision test apparatus, comprising:

a light-occluding casing;

test object carrying means mounted within said casing and having a plurality of test object carrying stations, adapted for carrying a plurality of vision test objects, each said test object carrying station including biasing means adapted for biasing a test object in a direction away from said test object carrying station, and retainer means adapted to retain said test object on said test object carrying station against the biasing of said bias means, said retainer means being switchable between a retain position where said test object is retained, and a release position where said test object is released from said retain position; and viewing means, coupled to said casing, for providing a viewing station from which one of said test object carrying stations is viewed.

8. Vision test apparatus comprising:

a light-occluding casing test object carrying means rotatably mounted within said casing and having a plurality of test object carrying stations, adapted for carrying a plurality of vision test objects, said carrying means having an end;

viewing means, coupled to said casing, for providing a viewing station from which one of said test object carrying stations is viewed;

cam wheel registration means, coupled to said carrying means end and having a plurality of registration devices, each such registration device corresponding to a respective one of said test object carrying stations; and registration detecting means, coupled to said casing, for detecting which of said plurality of test object carrying stations is visible from said viewing station and outputting a signal corresponding thereto.

9. Vision test apparatus, comprising:

a light-occluding casing test object carrying means mounted within said casing and having first, second and third test object carrying stations each adapted for carrying a vision test object, said carrying means being moveable so as to position one of said carrying stations at a viewing position;

viewing means coupled to said casing for providing a viewing station from which said viewing position is observable;

motor means for moving said carrying means; and remote control means, coupled to said motor means and located remotely from said casing and having a keypad adapted for remotely controlling said motor means, said remote control means having reset means for automatically controlling said motor means to cause said first test object carrying station to be positioned at said viewing position.

10. Apparatus according to claim 9 wherein said remote control means further includes power-on means for applying power to said motor means, and wherein activation of said power-on means causes said reset means to activate said motor means to automatically position said first test object carrying station at said viewing position.

11. Apparatus according to any one of claims 3, 4, 6, 7, 8 or 9 wherein said test object carrying means includes a drum having a first end rotatably mounted on said casing, and a second end having an open portion, and wherein said apparatus further includes illumination means, coupled to said casing and extending inside said drum through said open portion, for illuminating one of said test object carrying stations.

12. Apparatus according to claim 11 wherein each said test object carrying station includes a left and a right portion, and wherein said illumination means includes left and right illumination devices for illuminating said left and right portions, respectively.

13. Apparatus according to claim 11 wherein said illumination means is switchable between a bright illumination and a dim illumination which provides less light than said bright illumination.

14. Apparatus according to any one of claims 1, 4, 6, 7, 8 or 9 wherein said viewing means includes peripheral vision testing means for testing peripheral vision, said peripheral vision testing means including:

an illumination source providing light; and fiber optic means for carrying said light from said illumination means to a location on said viewing means from which peripheral vision is tested.

15. Apparatus according to claim 14 wherein said viewing means includes a left eye viewing port and a right eye viewing port, and wherein said peripheral vision testing means further includes:
- a plurality of locations adjacent said left and right viewing ports from which peripheral vision is tested; and
- a plurality of independent fiber optic means for respectively carrying light from said illumination source to respective ones of said plurality of locations.

16. Apparatus according to claim 15 wherein said peripheral vision testing means further includes location detector means adapted to detect when a test subject is improperly positioned with respect to said plurality of locations, said location detector means including:
- radiation means carried on said viewing means, for providing radiation across said left and right viewing ports; and
- receptor means carried on said casing, for receiving said radiation passing across said left and right viewing ports, and for providing a misalignment signal when said radiation is received.

17. Apparatus according to claim 16 further including override switch means coupled to said location detector means and said illumination means for switching off said illumination means in response to said misalignment signal.

18. Apparatus according to any one of claims 1, 3, 4, 7, 8 or 9 wherein said viewing means includes a left eye viewing port having a first lens with a first optical axis, and a right eye viewing port having a second lens with a second optical axis which is substantially parallel with said first optical axis, and wherein said apparatus further includes far/near vision switching means for switching a viewing range of said test object carrying stations between far vision range and near vision range, said far/near vision switching means including:
- an axle horizontally mounted to said viewing means and rotatable about a horizontal axis;
- third and fourth lenses having third and fourth optical axes, respectively, and mounted to said axle; and
- actuator means coupled to said axle, for rotating said third and fourth lenses about said horizontal axis between a first position where said third and fourth optical axes are substantially perpendicular to said first and second optical axes, respectively, and a second position where said third and fourth optical axes are substantially co-linear with said first and second optical axes respectively.

19. Apparatus according to claim 18 wherein said viewing means includes a supplemental lens port, and wherein said axle includes a supplemental lens passage passing through said horizontal axis, wherein said supplemental lens passage is registered with said supplemental lens port only when said third and fourth lenses are rotated to said first position.

20. Apparatus according to claim 19 further including supplemental lens means adapted to be inserted in said viewing means through said supplemental lens port and said supplemental lens passage, said supplemental lens means including fifth and sixth lenses having fifth and sixth optical axes, respectively, said fifth and sixth optical axes being substantially co-linear with said first and second optical axes respectively when said supplemental lens means is inserted in said viewing means.

21. Apparatus according to claim 18 wherein said far/near vision switching means further includes:
- a position registration device coupled to said axle and rotatable therewith; and
- position registration detecting means, coupled to said viewing means, for detecting a position of said position registration device and providing a position signal corresponding thereto.

22. Apparatus according to any one of claims 1, 3, 4, 6, 8, or 9 wherein said test object carrying means includes a plurality of test object retaining means, each located at one of said plurality of test object carrying stations and adapted to retain a test object on the corresponding carrying station, each said retaining means including:
- biasing means mounted in said test object carrying means, adapted for biasing a test object away from said test object carrying means; and
- holding means mounted on said test object carrying means, adapted for retaining said test object on said test object carrying means against said biasing of said biasing means, said clip means being adjustable to allow said test object to be moved away from said test object carrying means by said biasing means.

23. Apparatus according to any one of claims 1, 3, 6 or 7 wherein said test object carrying means includes a drum having a cam wheel fixed thereto, said cam wheel having a periphery with a plurality of registration devices spaced therearound, each registration device being located adjacent to a respective one of said plurality of test object carrying stations, and wherein said apparatus further includes detector means, coupled to said casing, for detecting said registration devices and providing a first location signal each time a registration device is detected.

24. Apparatus according to claim 23 wherein said cam wheel includes a datum registration device located adjacent one of said test object carrying stations, and wherein said detector means detects said datum registration device and provides a second location signal corresponding thereto.

25. Apparatus according to claim 24 further including indicator means, coupled to said detector means, for providing an indication signal indicating which of said plurality of test object carrying stations is located at a viewing position with respect to said viewing means.

26. Apparatus according to claim 25 further including:
- drive means, coupled to said casing, for rotatably driving said drum; and
- control means coupled to said casing and to said drive means and to said detector means and to said indicator means for controlling said drive means to drive said drum in accordance with said first and second location signals; and
- wherein said indicator means includes display means for displaying a signal indicating which test object carrying station is located at said viewing position.

27. Apparatus according to claim 26 further including computer interface means, coupled to said control means, adapted for interfacing said control means to a computer.

28. Apparatus according to claim 27 wherein said interface means includes an RS 232 interface.

29. Apparatus according to claim 26 wherein said indicator means is located remotely from said casing, and wherein said apparatus further includes remote control means, mounted to said indicator means, for remotely controlling said control means.

30. Apparatus according to any one of claims 1, 3, 4, 6, 7, 8 or 9 further including:
   a base pivotally mounted to said casing; and
   counterbalance bias means, coupled to said base and said casing, for temporarily fixing a pivot angle between said base and said casing.

31. Apparatus according to any one of claims 1, 3, 6, 7 or 8 further including motor means for rotatably driving said test object carrying means.

32. Apparatus according to any one of claims 1, 3, 4, 6, 7, 8 or 9 further including a vision test object coupled to one of said test object carrying stations, said test object including:
   first and second layers of glass;
   a test pattern interposed between said layers of glass;
   a light diffusing layer interposed between said layers and adjacent said test pattern.

* * * * *